United States Patent
Gurjar et al.

(10) Patent No.: US 10,556,851 B2
(45) Date of Patent: Feb. 11, 2020

(54) PROCESS FOR PREPARATION OF PROSTACYCLIN DERIVATIVES

(71) Applicant: Emcure Pharmaceuticals Limited, Bhosari, Pune (IN)

(72) Inventors: Mukund Keshav Gurjar, Pune (IN); Narendra Kumar Tripathy, Pune (IN); Chinmoy Mriganka Pramanik, Pune (IN)

(73) Assignee: Emcure Pharmaceutical Limited, Bhosari, Pune (IN)

( * ) Notice: Subject to any disclaimer, the term of this patent is extended or adjusted under 35 U.S.C. 154(b) by 0 days.

(21) Appl. No.: 16/071,967

(22) PCT Filed: Jan. 25, 2017

(86) PCT No.: PCT/IB2017/050381
§ 371 (c)(1),
(2) Date: Jul. 23, 2018

(87) PCT Pub. No.: WO2017/130109
PCT Pub. Date: Aug. 3, 2017

(65) Prior Publication Data
US 2019/0031589 A1    Jan. 31, 2019

(30) Foreign Application Priority Data

Jan. 27, 2016 (IN) .............................. 201621002907
Mar. 15, 2016 (IN) .............................. 201621008910

(51) Int. Cl.

| | |
|---|---|
| C07C 51/08 | (2006.01) |
| C07C 37/00 | (2006.01) |
| C07C 45/64 | (2006.01) |
| C07C 253/00 | (2006.01) |
| C07C 253/30 | (2006.01) |
| C07B 51/00 | (2006.01) |
| C07C 39/17 | (2006.01) |
| C07C 47/575 | (2006.01) |
| C07C 59/72 | (2006.01) |
| C07C 255/13 | (2006.01) |

(52) U.S. Cl.
CPC ............ *C07C 51/08* (2013.01); *C07C 37/002* (2013.01); *C07C 45/64* (2013.01); *C07C 253/30* (2013.01); *C07B 51/00* (2013.01); *C07B 2200/07* (2013.01); *C07C 39/17* (2013.01); *C07C 47/575* (2013.01); *C07C 59/72* (2013.01); *C07C 255/13* (2013.01); *C07C 2603/14* (2017.05)

(58) Field of Classification Search
CPC ....... C07C 51/08; C07C 37/002; C07C 41/28; C07C 45/64; C07C 45/673; C07C 253/30
See application file for complete search history.

(56) References Cited

U.S. PATENT DOCUMENTS

| | | |
|---|---|---|
| 6,441,245 B1 | 8/2002 | Moriarty et al. |
| 6,528,688 B2 | 3/2003 | Moriarty et al. |
| 6,700,025 B2 | 3/2004 | Moriarty et al. |
| 6,765,117 B2 | 7/2004 | Moriarty et al. |
| 8,242,305 B2 | 8/2012 | Batra et al. |
| 2002/0173672 A1 | 11/2002 | Moriarty et al. |

FOREIGN PATENT DOCUMENTS

| | | |
|---|---|---|
| CN | 1494524 | 5/2004 |
| WO | 2002053517 | 7/2002 |
| WO | 2014/203278 | 12/2014 |
| WO | 2016055819 | 4/2016 |

OTHER PUBLICATIONS

Node et al., "Hard Acid and Soft Nucleophile System. 2. Demethylation of Methyl Ethers of Alcohol and Phenol with an Aluminium Halide-Thiol System," J. Org. Chem. (1980), 45(22): 4275-4277, abstract.

Vutukuri et al., "A Mild Deprotection Strategy for Allyl-Protecting Groups and Its Implications in Sequence Specific Dendrimer Synthesis," J. Org. Chem. (2002), 68 (3): 1146-1149, table 1.

*Primary Examiner* — Sikarl A Witherspoon
(74) *Attorney, Agent, or Firm* — Florek & Endres PLLC

(57) ABSTRACT

The invention relates to improved method of synthesis for Treprostinil comprising condensation reaction of the carbonyl compound having allyl, alkyl, crotyl or MEM-protected phenolic hydroxyl group, compound (4) with a hydroxyl-protected alkynol (5) to give the condensation product, compound (6). Subjecting compound (6) to oxidation, reduction, hydroxyl protection and carbonylation, cyclization reactions gave the tricyclic derivative (10). Further reactions comprising reduction, hydrogenation and deprotection of the phenolic and side-chain hydroxyl groups, wherein the sequence and choice of reagents was governed by protecting groups, gave the triol intermediate, compound (14). Cyanoalkylation at phenolic hydroxyl functionality and further hydrolysis yielded the prostacyclin compound, Treprostinil (1) and its pharmaceutically acceptable salts, having desired purity.

12 Claims, No Drawings

PROCESS FOR PREPARATION OF PROSTACYCLIN DERIVATIVES

This application is the U.S. National Stage filing of International Patent Application Number PCT/IB2017/050381 which claims the benefit of Indian Provisional Applications No. 201621002907, filed on 27 Jan. 2016, and 201621008910, filed on 15 Mar. 2016, which are hereby incorporated by reference in entirety.

FIELD OF THE INVENTION

The present invention relates to an improved process for the synthesis of prostacyclin derivatives like Treprostinil (1) and its pharmaceutically acceptable salts, wherein suitable hydroxyl protection of the phenolic derivative of formula (3) with an unsaturated alkyl leads to regulation of impurities and utilization of a appropriate deprotecting agent yields prostacyclin derivative, Treprostinil (1) and its pharmaceutically acceptable salts conforming to regulatory limits.

BACKGROUND OF THE INVENTION

Prostacyclin analogues are known to exhibit therapeutic effects related to inhibition of platelet aggregation, lesions inhibition, reduction in gastric secretion, bronchodilation etc. Treprostinil (1) and its pharmaceutically acceptable salts, chemically known as (1R,2R,3aS,9aS)-[[2,3,3a,4,9,9a-hexahydro-2-hydroxy-1-[(3S)-3-hydroxyoctyl]-1H-benz[f] inden-5-yl]oxy]acetic acid, is a stable synthetic analogue of prostacyclin ($PGI_2$), belonging to the benzindene prostacyclin class of compounds. USFDA approved formulations such as Remodulin (infusion), Tyvaso (for inhalation) have Treprostinil (1) and its pharmaceutically acceptable salts, as the active ingredient for inducing vasodilation during the treatment of pulmonary arterial hypertension.

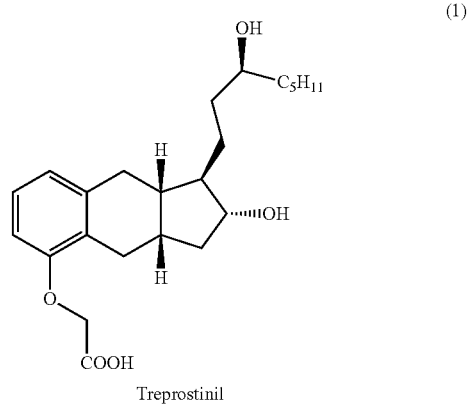

Treprostinil

The synthesis of Treprostinil (1) was first disclosed in U.S. Pat. No. 4,306,075 and since then different synthetic strategies for this molecule have been disclosed in various patents such as U.S. Pat. Nos. 6,441,245, 6,528,688, 6,700,025, 6,765,117, 6,809,223, 8,242,305 etc. The scheme for method of synthesis as disclosed in U.S. Pat. No. 6,765,117 is given below.

Scheme 1: Treprostinil synthesis scheme, as disclosed in US 6,765,117

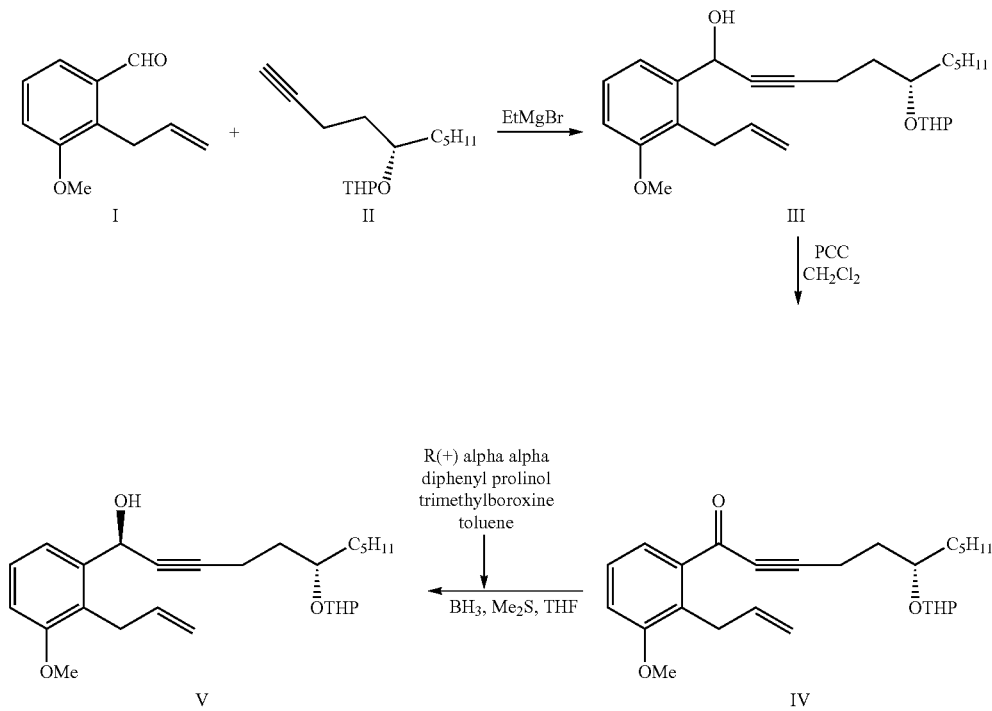

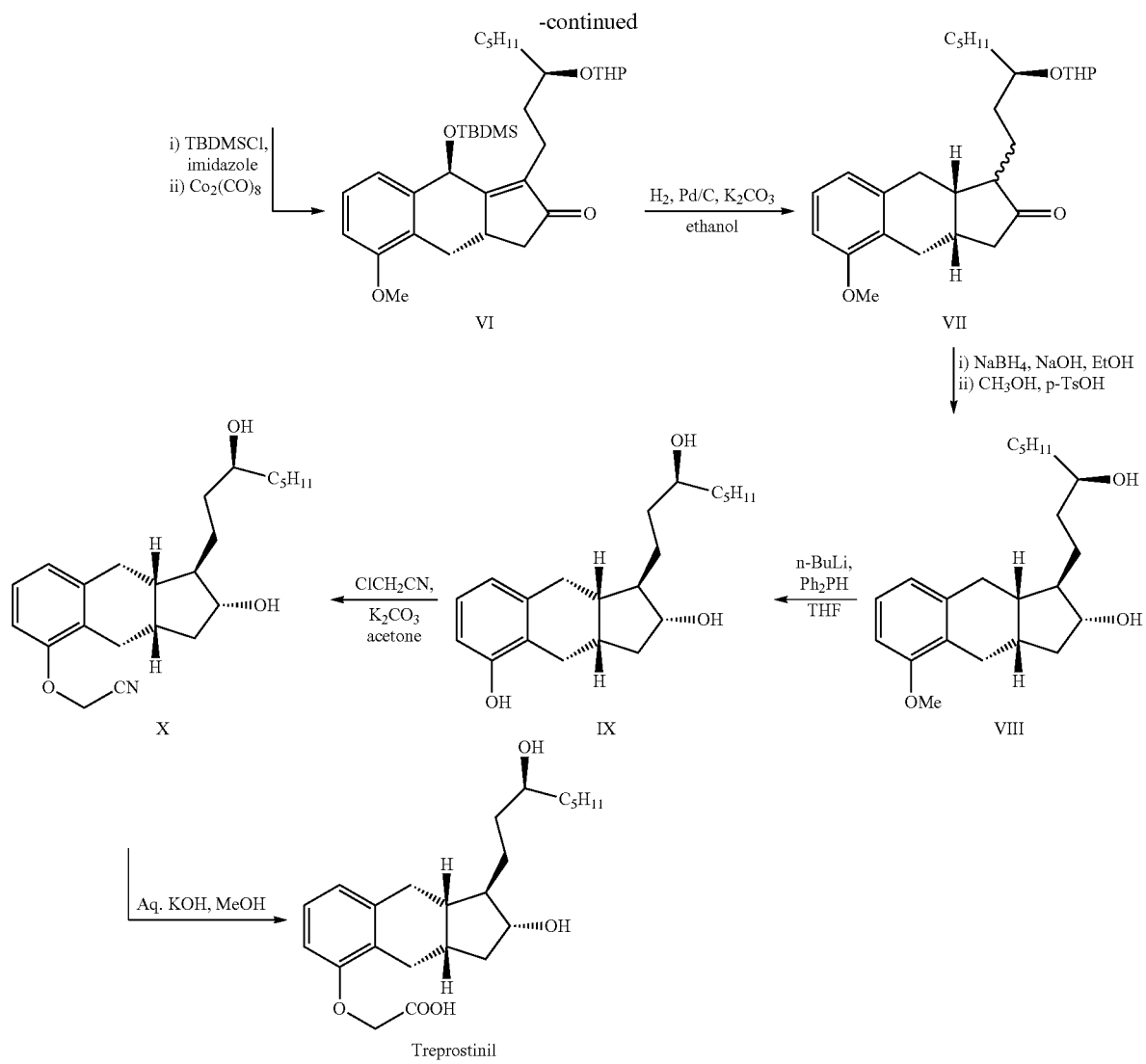

Most of the synthetic methods described in the aforementioned references resort to expensive, hazardous reagents and tedious condensation, deprotection and separation procedures at various intermediate stages of synthesis. For example, U.S. Pat. No. 6,441,245 discloses deprotection of alkyl-protected phenolic hydroxyl group in treprostinil using n-butyl lithium and diphenyl phosphine. These hazardous reagents require stringent anhydrous conditions and pose operational difficulties, especially when used on industrial scales.

WO2016055819 discloses a process wherein the $C_5H_{11}$ side chain is added in the later stage of synthetic sequence. The process comprises condensation of aldehyde and alkyne derivatives, followed by subsequent reactions to give the tricyclic intermediate and further reactions including Wittig reaction, stereoselective carbonyl reduction, deprotection etc. for the introduction of $C_5H_{11}$ side chain.

Various protecting functionalities for the phenolic hydroxyl group have been disclosed in prior art. However, the inventors observed that considering the complex, multi-step synthetic sequence, highly acid-labile, bulky protecting groups such as triphenylmethyl (trityl) were not feasible on a commercial scale. Also, use of protecting agents such as tertiary butyldimethylsilyl (TBDMS) for the phenolic hydroxyl either necessitated very specific reagents like tetra n-butyl ammonium fluoride (TBAF) or high pressure hydrogenation conditions for deprotection.

Hence, there was a need for a practical and economical synthetic process for Treprostinil which comprised use of appropriate, easily removable hydroxyl protecting groups that would decrease the level of associated impurities in the reactions. Deprotection of the hydroxyl group could be done at appropriate stages with mild and selective reagents to achieve the desired conversions. It was found that reactions of phenolic hydroxyl substrates protected with unsaturated alkyl like allyl, crotyl, propargyl had a better impurity profile as compared to other protecting groups as the reactions were facile, provided higher yields and the impurities were below the usual limits. Also, the intermediate products with unsaturated alkyl as protecting group that were isolated had a better impurity profile and did not require any further purification, thus avoiding additional steps and lowering the overall costs.

The present inventors have developed an efficient and economical process for synthesis of Treprostinil (1) and its pharmaceutically acceptable salts, overcoming the problems faced in the prior art, by utilizing alkyl or unsaturated alkyl groups as protecting agents for the phenolic hydroxyl group. The use of appropriate hydroxyl protecting groups like alkyls, allyl, crotyl, MEM and selective deprotecting reagents like tetrakis triphenylphosphine palladium, aluminium chloride/decanethiol, helped in controlling the impurity formation at various intermediate stages and provided the desired molecule with significant improvement in yield.

OBJECT OF THE INVENTION

An objective of the present invention is to provide an industrially applicable, convenient process for synthesis of Treprostinil (1) and its pharmaceutically acceptable salts, which regulates the formation of impurities and does not require elaborate purification methods.

Another object of the invention relates to the use of hydroxyl protecting groups such as unsaturated alkyls such as allyl, crotyl, propargyl; alkoxyalkyl groups like 2-methoxyethoxymethyl (MEM), Methoxymethyl ether (MOM), alkyl and arylalkyl groups, which are easily deprotected, and in turn reduces the formation of impurities during protection and deprotection stages and yields intermediates as well as the final active pharmaceutical ingredient with desired purity.

SUMMARY OF THE INVENTION

An aspect of the invention relates to an improved process for the preparation of Treprostinil (1) and its pharmaceutically acceptable salts, comprising reacting phenolic aldehyde of formula (4) protected with unsaturated alkyl, alkyl, arylalkyl or alkoxyalkyl group with alkyne derivative of formula (5) to give compound (6), further oxidation to provide compound (7), asymmetric reduction followed by protection of the hydroxyl group of the resulting compound (8) to give compound (9), cyclization in presence of a carbonylating agent to give compound (10), further dehydroxylation, hydrogenation and subsequent reduction to give compound (12), followed by deprotection of the side chain and phenolic hydroxyl functions to give compound (14) and subsequent cyanoalkylation followed by hydrolysis and acidification to provide Treprostinil (1) and its pharmaceutically acceptable salts.

DETAILED DESCRIPTION OF THE INVENTION

While carrying out extensive experimentation aimed at designing a convenient, industrially applicable synthetic strategy for Treprostinil (1) and its pharmaceutically acceptable salts, the present inventors surprisingly found that when the hydroxyl protecting group in compound (4) was selected from unsaturated alkyls such as allyl, crotyl, propargyl or alkoxyalkyl ethers such as 2-methoxyethoxymethyl (MEM), Methoxymethyl ether (MOM), arylalkyl groups such as substituted and unsubstituted benzyl or alkyl groups such as methyl, ethyl, or tertiary butyl, all the reactions involving the protected phenolic hydroxy group, such as condensation between the carbonyl derivative (4) and the protected alkynol (5) were facile with impurity profile below limit and selectively provided the intermediate products in good yield. Further deprotection of these groups at an appropriate stage of Treprostinil synthesis was also easy in comparison to the prior art processes. Formation of undesired side products, associated impurities was brought under control and as a result, the desired molecule Treprostinil and its pharmaceutically acceptable salts was obtained in good overall yield as compared to the methods disclosed in prior art.

The term 'alkyl' as used herein refers to a hydrocarbon radical which can be either straight chain or branched having from 1 to 8 carbon atoms Non-limiting examples include methyl ethyl, propyl, butyl etc.

The term "aryl" as used herein refers to unsaturated, aromatic cyclic radicals having 6 to 14 carbon atoms. The aryl can be a single aromatic ring or multiple aromatic rings that are fused together. Non-limiting examples include phenyl, biphenyl, naphthyl, anthracenyl, tetrahydronapthyl, indanyl and phenanthryl.

The term "arylalkyl" as used herein refers to an aryl group as defined above directly bonded to an alkyl group as defined above which is attached to the main molecule. Examples include but are not limited to —$CH_2C_6H_5$, and —$C_2H_5C_6H_5$. The arylalkyl group is either substituted or unsubstituted. Non-limiting examples for substituted arylalkyl group include aryl substituted with methoxy, nitro, halo, alkyl and others.

The term "alkoxyalkyl" as used herein refers to an alkoxy group attached to an alkyl group which is further attached with the main molecule.

Pharmaceutically acceptable salts of Treprostinil comprise a Group IA or IIA metal, K, Ca, Na, Ba, Li, Mg or Cs and diethanolamine.

In an embodiment, as disclosed in scheme 2, meta hydroxy benzaldehyde was treated with allyl bromide in presence of a base like potassium carbonate to give allyloxy aldehyde derivative, compound (2), which was then subjected to thermal rearrangement between 170 to 210° C. using decahydronaphthalene as solvent to give compound (3), which was then treated with a hydroxyl protecting reagent to give compound (4). The protecting group R was selected from the group comprising unsaturated alkyls like allyl, crotyl, propargyl etc., alkoxy-alkyl groups such as 2-methoxy ethoxymethyl (MEM), MOM, arylalkyl groups such as substituted and unsubstituted benzyl wherein substitutent is selected from methoxy, alkyl, halogen and alkyl groups such as methyl, ethyl, tertiary butyl, but preferably, allyl (—$CH_2$—CH=$CH_2$), crotyl (—$CH_2$—CH=CHCH$_3$), Propargyl and 2-methoxyethoxymethyl (MEM), MOM, p-methoxy benzyl, p-nitrobenzyl and others.

Scheme 2: Method of preparation of intermediate (10)

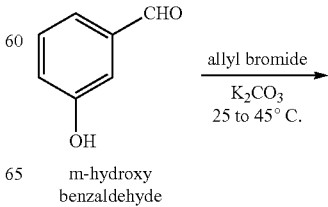

m-hydroxy benzaldehyde

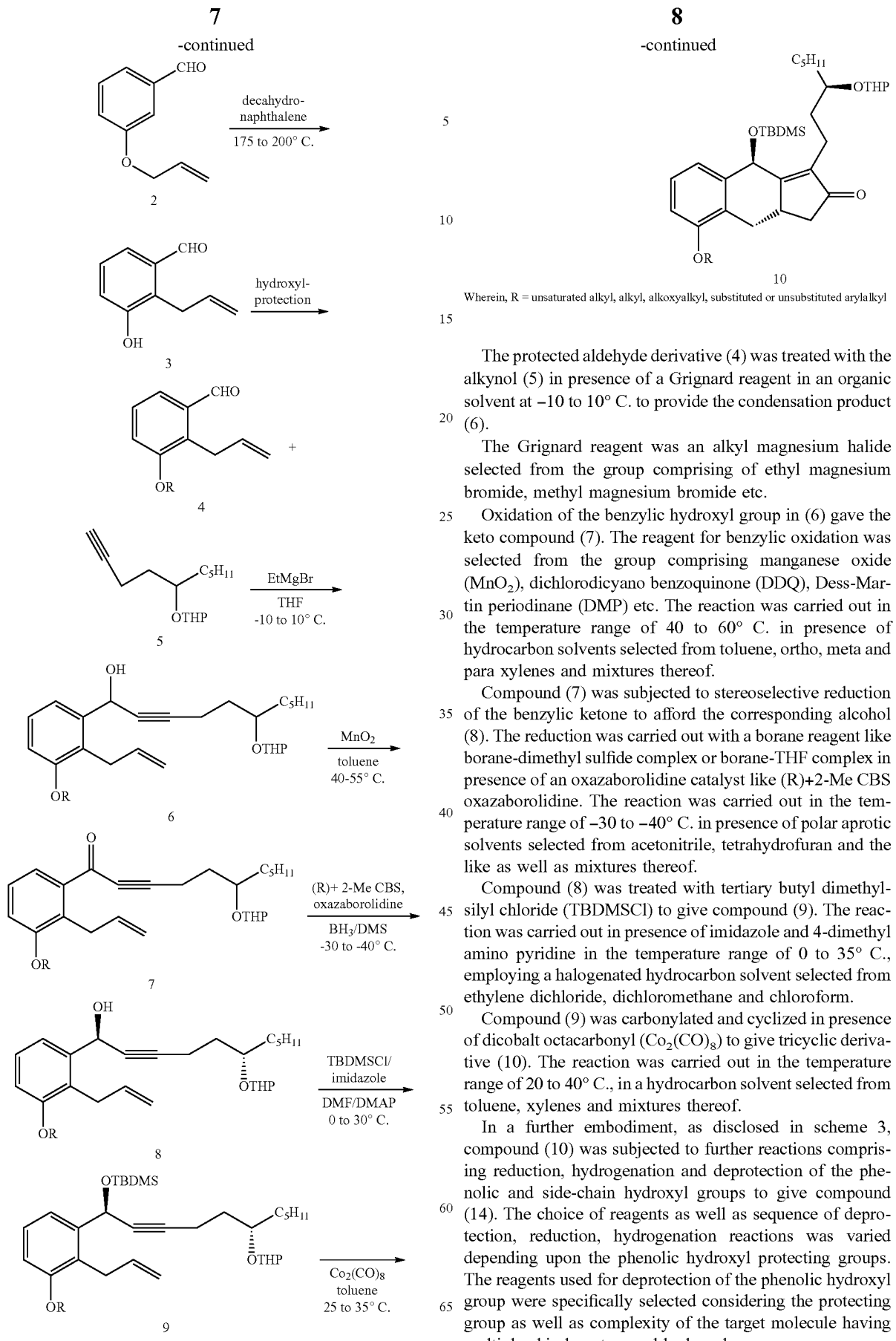

Wherein, R = unsaturated alkyl, alkyl, alkoxyalkyl, substituted or unsubstituted arylalkyl The protected aldehyde derivative (4) was treated with the alkynol (5) in presence of a Grignard reagent in an organic solvent at −10 to 10° C. to provide the condensation product (6).

The Grignard reagent was an alkyl magnesium halide selected from the group comprising of ethyl magnesium bromide, methyl magnesium bromide etc.

Oxidation of the benzylic hydroxyl group in (6) gave the keto compound (7). The reagent for benzylic oxidation was selected from the group comprising manganese oxide ($MnO_2$), dichlorodicyano benzoquinone (DDQ), Dess-Martin periodinane (DMP) etc. The reaction was carried out in the temperature range of 40 to 60° C. in presence of hydrocarbon solvents selected from toluene, ortho, meta and para xylenes and mixtures thereof.

Compound (7) was subjected to stereoselective reduction of the benzylic ketone to afford the corresponding alcohol (8). The reduction was carried out with a borane reagent like borane-dimethyl sulfide complex or borane-THF complex in presence of an oxazaborolidine catalyst like (R)+2-Me CBS oxazaborolidine. The reaction was carried out in the temperature range of −30 to −40° C. in presence of polar aprotic solvents selected from acetonitrile, tetrahydrofuran and the like as well as mixtures thereof.

Compound (8) was treated with tertiary butyl dimethylsilyl chloride (TBDMSCl) to give compound (9). The reaction was carried out in presence of imidazole and 4-dimethyl amino pyridine in the temperature range of 0 to 35° C., employing a halogenated hydrocarbon solvent selected from ethylene dichloride, dichloromethane and chloroform.

Compound (9) was carbonylated and cyclized in presence of dicobalt octacarbonyl ($Co_2(CO)_8$) to give tricyclic derivative (10). The reaction was carried out in the temperature range of 20 to 40° C., in a hydrocarbon solvent selected from toluene, xylenes and mixtures thereof.

In a further embodiment, as disclosed in scheme 3, compound (10) was subjected to further reactions comprising reduction, hydrogenation and deprotection of the phenolic and side-chain hydroxyl groups to give compound (14). The choice of reagents as well as sequence of deprotection, reduction, hydrogenation reactions was varied depending upon the phenolic hydroxyl protecting groups. The reagents used for deprotection of the phenolic hydroxyl group were specifically selected considering the protecting group as well as complexity of the target molecule having multiple chiral centers and hydroxyl groups.

Scheme 3: Method for the preparation of Treprostinil (1) and its pharmaceutically acceptable salts,

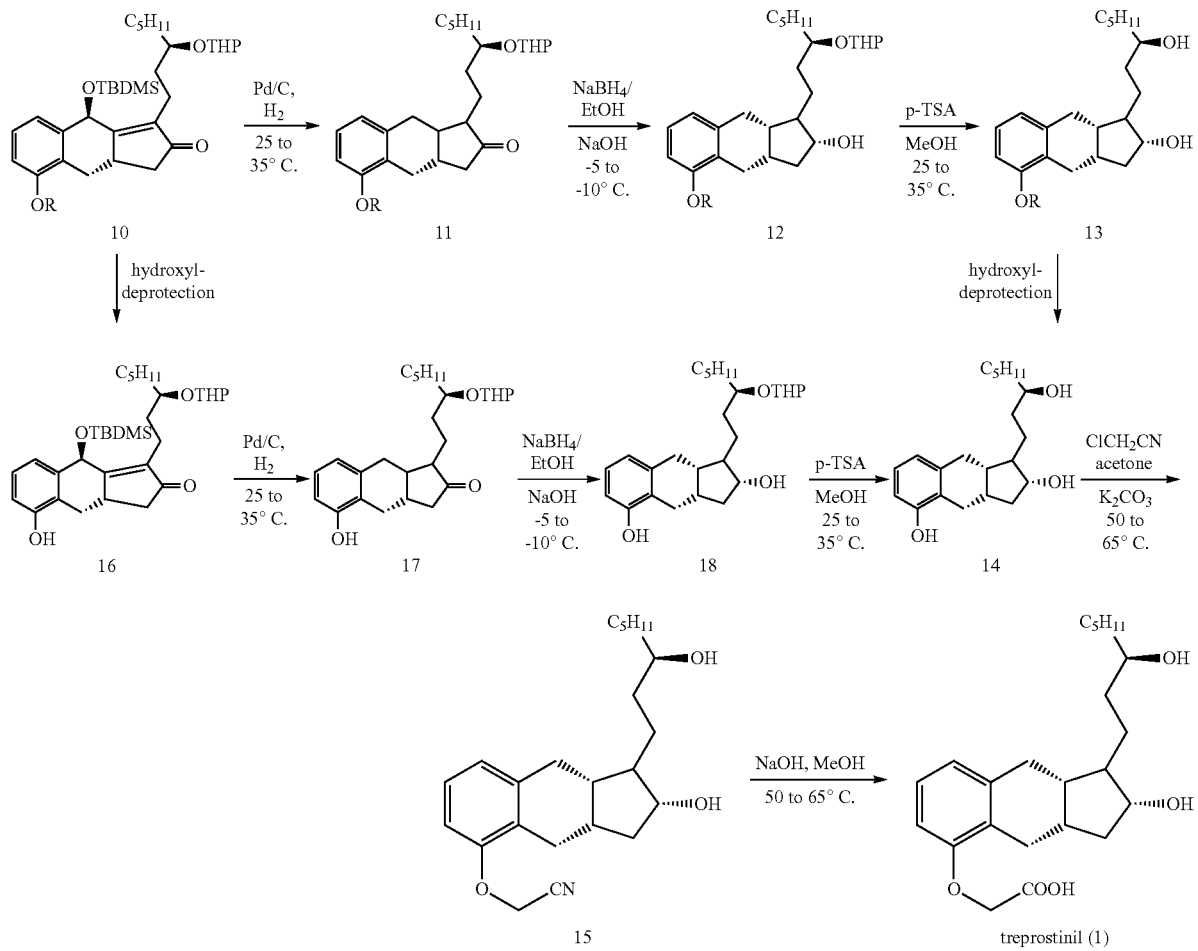

Wherein, R = unsaturated alkyl, alkyl, alkoxyalkyl, substituted or unsubstituted arylalkyl When the protecting group was selected from unsaturated alkyl such as allyl, crotyl, compound (10) was first subjected to hydroxyl deprotection in presence of a palladium reagent to give compound (16). Further dehydroxylation of TBDMS protected hydroxyl group under hydrogenation conditions like gaseous hydrogen in presence of noble metal catalysts gave compound (17), which, after reduction employing sodium borohydride gave compound (18). Deprotection of the side-chain hydroxyl group in (18) in presence of a acid such as p-toluenesulfonic acid gave the desired intermediate, compound (14).

In a further embodiment, as disclosed in scheme 3, when the protecting group was selected from alkyls such as methyl, ethyl, tertiary butyl, or an arylalkyl group like benzyl, p-methoxybenzyl, p-nitrobenzyl compound (10) was first subjected to hydrogenation conditions for dehydroxylation of TBDMS protected hydroxyl to give ketone compound (11), which after borohydride reduction provided alcoholic derivative, compound (12). Further treatment of compound (12) using acids like p-toluenesulfonic acid for deprotection of tetrahydropyran group gave compound (13), wherein the alkyl deprotection was carried out using reagents such as $AlCl_3$/decanethiol, $AlCl_3$/thiourea, to provide compound (14). Deprotection with $AlCl_3$/decanethiol or palladium tetrakis resulted in a facile reaction with improved impurity profile as compared to other deprotecting agents.

The phenolic hydroxyl group in compound (14) thus obtained was further substituted using haloacetonitriles such as chloroacetonitrile or bromoacetonitrile, in presence of potassium carbonate to give compound (15), followed by hydrolysis of the nitrile functionality using bases like sodium, potassium or lithium hydroxide to yield the desired compound, Treprostinil (1). Treprostinil so obtained was converted to its alkali metal salt like Treprostinil sodium using alkali metal hydroxide such as sodium hydroxide.

Scheme 4A: Method of preparation of intermediate (6α)

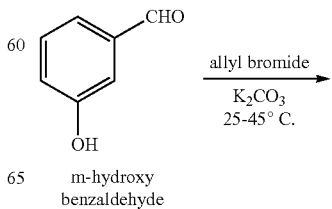

m-hydroxy benzaldehyde

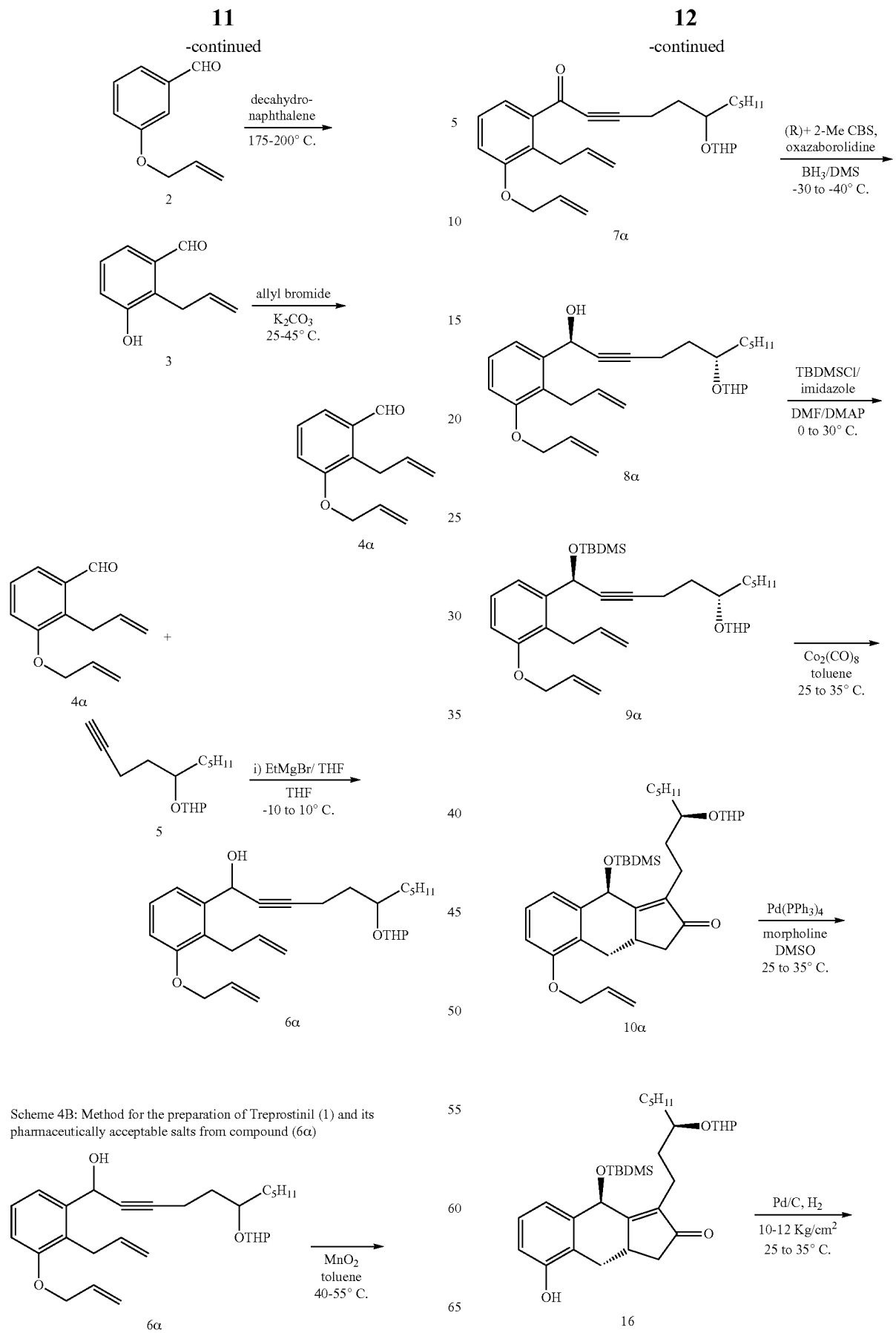

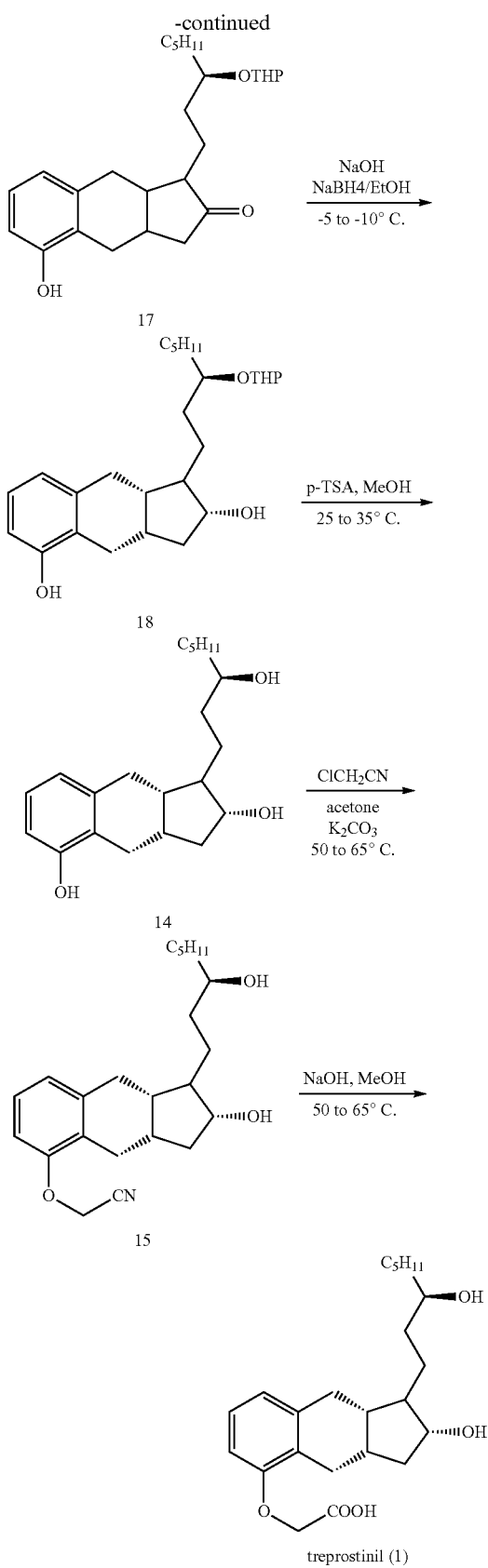

with allyl group, compound (3), synthesized as given above, was subjected to reaction with allyl bromide in presence of a base like potassium carbonate to give compound (4α), which, when treated with the protected alkynol (5) in presence of ethyl magnesium bromide provided the condensation product compound (6α). Benzylic oxidation of compound (6α) using $MnO_2$, followed by asymmetric reduction of the resulting ketone, compound (7α) employing (R)(+) 2-Me CBS oxazaborolidine and borane-dimethyl sulfide complex provided the corresponding alcohol, compound (8α). As mentioned above, protection of the hydroxyl group using TBDMSCl gave compound (9α), which, after carbonylation and cyclization with $Co_2(CO)_8$ provided compound (10α).

The tricyclic compound (10α) was first subjected to deprotection of the allyl group to give compound (16). The reaction was carried out in the temperature range of 20 to 70° C. using tetrakis triphenylphosphine palladium, $Pd(PPh_3)_4$ in presence of a base like morpholine, potassium carbonate, sodium 2-ethyl hexanoate and in a solvent selected from dimethyl sulfoxide (DMSO), methanol, dichloromethane, ethyl acetate and combinations thereof. In particular, the allyl deprotection was done using $Pd(PPh_3)_4$, morpholine, solvent DMSO wherein the temperature was between 20 to 40° C.

Compound (16) was subjected to dehydroxylation of TBDMS protected hydroxyl employing hydrogenation conditions in presence of transition metal catalysts using alcoholic solvents selected from methanol, ethanol, isopropanol etc. in the temperature range of 20 to 40° C. to give the ketone compound (17). Further reduction of compound (17) using borohydrides selected from sodium borohydride, potassium borohydride in presence of alcohol solvent such as ethanol, methanol, isopropanol provided dihydroxyl intermediate, compound (18).

Deprotection of hydroxyl group in the side chain was carried out using acids such as p-toluene sulfonic acid and alcoholic solvents selected from methanol, ethanol, isopropanol etc. in the temperature range of 20 to 40° C. to give the trihydroxy derivative, compound (14), which was converted to treprostinil following the process mentioned before. The same sequence of reactions was followed when the phenolic hydroxyl was protected with other unsaturated alkyl groups like the crotyl (—$CH_2$—CH=$CHCH_3$), propargyl group. Compound (14) was then converted to Treprostinil and its pharmaceutically acceptable salts using conventional methods.

In yet another embodiment, when the phenolic hydroxyl was protected with alkyl group such as methyl group, the corresponding tricyclic compound (10β), (Scheme 2 and 3, compound 10, R=Me) was first subjected to dehydroxylation and reduction reactions using $H_2$, Pd/C and sodium borohydride respectively, followed by deprotection of the side-chain hydroxyl functionality using para-toluene sulfonic acid to give the alkoxyphenyl benzindene diol derivative, compound (13β) (Schemes 2 and 3, compound 13, R=Me), which was then subjected to deprotection of substituted phenolic hydroxyl group. The cleavage of phenyl-alkyl ether linkage in compound (13β) was carried out using reagents such as metal halide/thiol, $AlCl_3$/thiourea, sodium sulfide, HBr/acetic acid, sodium methoxide/dodecane thiol etc. The thiol derivative was selected from ethanethiol, decanethiol, dodecanethiol and the metal halide (Lewis acid) was selected from aluminium chloride and aluminium bromide, wherein, in particular, $AlCl_3$/decanethiol combination was used. The resultant compound (14) was then converted to In a further embodiment, as disclosed in Scheme 4A & Scheme 4B, wherein the phenolic hydroxyl was protected treprostinil having moisture content less than 0.5%, and subsequently to its therapeutically acceptable salts.

Similarly, with 2-methoxyethoxymethyl (MEM), as the phenolic hydroxyl protecting group, compound (10γ) (Schemes 2 and 3, compound 10, R=MEM) was first reduced and dehydroxylated using H2, Pd/C, followed by sodium borohydride reduction to give the MEM protected benzindene diol derivative, compound (12γ), which was followed by deprotection of the side-chain hydroxyl functionality using para-toluene sulfonic acid to give compound (13γ) (Schemes 2 and 3, compound 13, R=MEM). The alkoxyphenyl benzindene diol derivative, (13γ) was then subjected to deprotection of the MEM group using acids like hydrobromic acid, formic acid, trifluoroacetic acid etc. or pyridinium p-toluenesulfonate/tertiary butanol, or carbon tetrabromide in isopropyl alcohol to give compound (14).

It was observed that when the phenolic hydroxyl protecting group was an alkyl group, stronger reaction conditions like $BCl_3$, $BBr_3$, $Ph_2PH$/n-BuLi, were required for the deprotection. For allyl protected phenols, on the other hand, the deprotection conditions were milder which controlled the associated undesired reactions. Consequently, the impurity profiles for deprotection and subsequent reactions were significantly improved, and treprostinil having desired purity was obtained in almost more than 10-15% higher yield as compared to alkyl protected phenol route.

In yet another embodiment, as depicted in Scheme-5, the racemic tricyclic derivative, compound (10A), wherein R is selected from allyl, crotyl, propargyl, MEM and MOM and substituted or unsubstituted arylalkyl; was directly obtained from the racemic alcohol, compound (6). The alcohol was protected using TBDMSCl in presence of imidazole to give compound (9A), which on further reaction with $Co_2(CO)_8$ provided compound (10A). It was further subjected to sequence of dehydroxylation and reduction reactions in presence of transition metal catalyzed hydrogenation, borohydride reduction as disclosed earlier in Scheme 3. This was followed by deprotection of tetrahydropyran group in the side chain using para-toluene sulfonic acid to give the racemic dihydroxy derivative, compound (13A) comprising a protected phenolic hydroxyl group. Treatment of compound (13A) with n-heptane which included heating to 60-70° C., cooling to room temperature, stirring and filtration separated the desired enantiomer as solid. Compound (13A), after deprotection of the phenolic hydroxyl group, employing the methods mentioned herein, furnished the enantiomerically pure compound (14). Compound (14) was converted to Treprostinil and its pharmaceutically acceptable salts.

Scheme 5: Method for the preparation of compound (14)

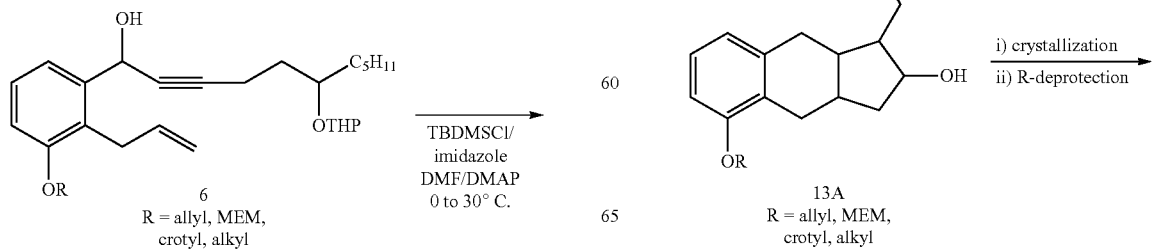

17
-continued

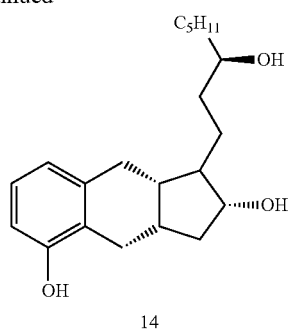

14

In yet another embodiment, as depicted in Scheme-6, compound (7) (disclosed in scheme 2) was prepared following an alternative route.

Scheme 6: Method for the preparation of compound (7)

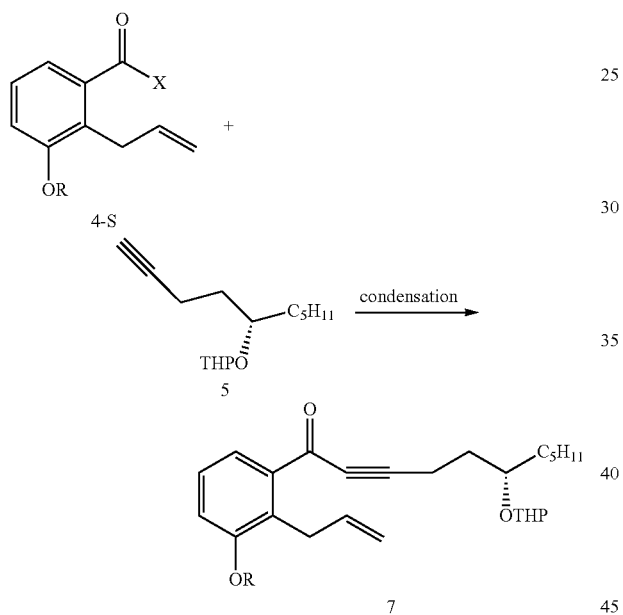

The compound (4-S) wherein the hydroxyl protecting group R is selected from the groups comprising allyl, MEM, MOM, crotyl, prppargyl, substituted or unsubstituted arylalkyl, alkyl etc., and X is selected from halogen, hydroxyl, alkoxy, unsubstituted amine, substituted amine etc. was reacted with the hydroxyl protected acetylene compound, (5). The resultant carbonyl compound (7) was then subjected to reactions as disclosed in Schemes 2 and 3 to obtain Treprostinil, which was then converted to its therapeutically acceptable salts.

The use of compound (4-S) as starting material in the Treprostinil synthetic sequence circumvented the use of hazardous and harsh reagent like PCC for oxidation as disclosed in the prior art. With X=Cl, the acid chloride derivative of compound (4-S) was treated with acetylene compound in presence of Pd(PPh$_3$)$_2$Cl$_2$, Copper iodide and triethyl amine to directly give the corresponding ketone, compound (7), eliminating the synthesis of hydroxyl derivative, compound (6), and associated oxidation reaction.

18

The hydroxyl-protected acetylene derivative, compound (5) was prepared following the process known in the art. Details of the synthetic steps for compound (5) are given in Scheme 7.

Scheme 7: Method for the preparation of compound (5)

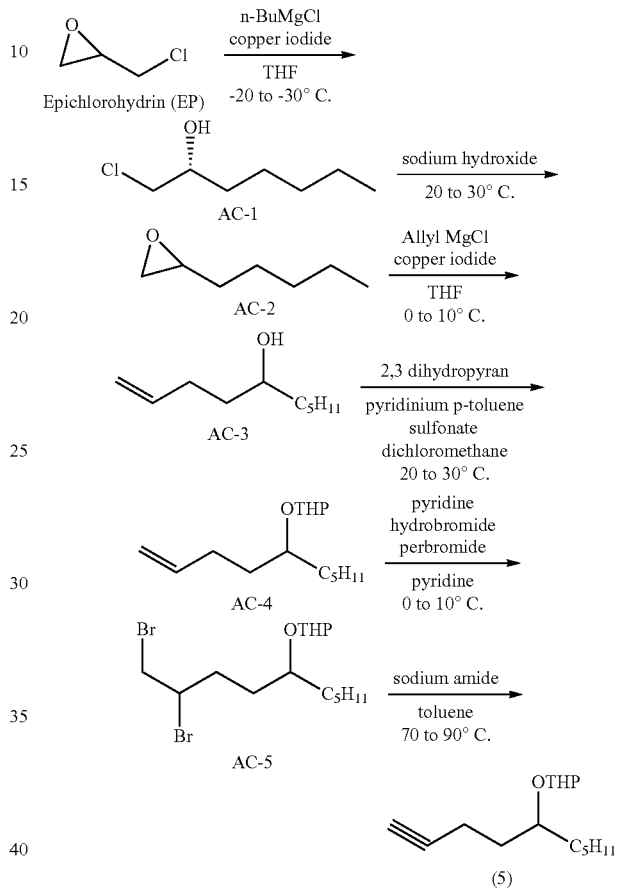

The following examples are meant to be illustrative of the present invention. These examples exemplify the invention and are not to be construed as limiting the scope of the invention.

EXAMPLES

Example 1

Synthesis of Compound (6α)

Ethyl magnesium bromide solution (143 ml, 3 M solution in THF was gradually added to the solution of compound (5) (110 g) in dry tetrahydrofuran (THF, 1000 ml). The reaction mixture was stirred at 55 to 65° C. The mass was then cooled to −10 to 0° C., and solution of compound (4α) (73.2 g in 110 ml THF) was slowly added to it under stirring. The reaction was continued at −10 to 0° C. till completion of the reaction, as monitored by HPLC. After completion of the reaction, the reaction mixture was quenched with gradual addition of aqueous ammonium chloride solution (110 gms ammonium chloride in 550 ml water). Ethyl acetate was added to the stirred reaction mixture and temperature was raised to 25 to 30° C. Separation and concentration of the organic layer gave crude mass which was subjected to column chromatographic purification using Silica gel as stationary phase and mixture of cyclohexane/ethyl acetate with variable polarity as eluent to provide compound (6α).

Yield: 118.2 g (72%)

$^1$H NMR (300 MHz, DMSO-D$_6$): δ7.17 (m, 2H), 6.89 (m, 1H), 6.03 (m, 1H), 5.90 (m, 1H), 5.73 (m, 1H), 5.37 (m, 2H), 5.22 (m, 1H), 4.91 (d, J=9.84 Hz, 2H), 4.53 (m, 3H), 3.74 (m 1H), 3.58 (m, 1H), 3.48 (m, 2H), 3.32 (m, 1H), 2.23 (m, 2H), 1.76-1.22 (m, 16H), 0.85 (t, J=5.3 Hz, 3H).

$^{13}$C NMR (75 MHz, DMSO-D$_6$): δ155.8, 141.8, 136.6, 133.8, 126.7, 126.6, 124.9, 124.8, 118.9, 118.91, 118.8, 116.5, 114.6, 111.2, 97.9, 97.8, 96.9, 84.8, 84.5, 82.01, 82.0, 81.7, 75.3, 74.7, 74.73, 68.3, 62.0, 60.0, 34.3, 33.7, 32.7, 32.4, 32.3, 31.3, 31.3, 30.7, 29.2, 25.03, 25.0, 24.5, 24.1, 22.02, 22.0, 19.7, 19.65, 19.6, 14.6, 14.1, 13.8, 13.7.

(M$^+$Na): 463.3

Example 2

Synthesis of Compound (7α)

Manganese dioxide (104.9 g) was added to the solution of compound (6α) (50 g in 225 ml toluene) and the reaction mixture was stirred at 45 to 50° C. till completion of the reaction, as monitored by HPLC. After completion, the reaction mixture was cooled, filtered, and concentrated to afford compound (7α). Yield: 101.0 g (96.7%)

Example 3

Synthesis of Compound (9α)

The solution of (R)-(+)-2-Methyl-CBS-oxazaborolidine (103.2 ml, 1M solution in Toluene) was added to the stirred solution of Compound (7α) (35.5 g) in tetrahydrofuran (142 ml) at 25 to 30° C. and stirring was continued at the same temperature. The reaction mass was then cooled to −30 to −40° C. and borane-dimethyl sulfide complex (BH$_3$/DMS, 10M, 17.2 ml) was added to it with continued stirring. The reaction was monitored by HPLC.

After completion of the reaction, the reaction mixture was warmed to −25 to −15° C. and methanol (71 ml) was slowly and cautiously added to it. The temperature of the reaction mass was raised to 25 to 30° C., followed by further stirring. The mixture was then cooled to 0 to 5° C. and ammonium chloride solution (5%, 177.5 ml) was added to it under stirring. The resulting mixture was extracted with methyl tertiary butyl ether. Separation and concentration of the organic layer gave a residue containing compound (8α).

Tertiary butyl dimethyl chlorosilane (TBDMSCl, 19.4 g) and imidazole (14.6 g) were added to the solution of compound (8α) in dichloromethane (355 ml), dimethyl form amide (3.6 ml) and 4-dimethyl amino pyridine (0.74 g). The reaction mixture was stirred at 25 to 30° C. After completion of reaction, as monitored by HPLC, the reaction mixture was quenched with water and organic layer was separated. Concentration of the organic layer followed by chromatographic purification yielded compound (9α). Yield: 37.8 g (84%)

$^1$H NMR (300 MHz, CDCl$_3$): δ7.26 (m, 1H), 7.17 (m, 1H), 6.78 (d, J=6.1 Hz, 1H), 6.09-5.91 (m, 2H), 5.58 (s, 1H), 5.41 (m, 1H), 5.24 (m, 1H), 5.01-4.95 (m, 2H), 4.62-4.51 (m, 3H), 3.88 (m, 1H), 3.65 (m, 2H), 3.54 (m, 1H), 3.43 (m, 1H), 2.32 (m, 1H), 2.23 (m, 2H), 1.86-1.21 (m, 15H), 0.93-0.86 (m, 12H), 0.12 (s, 3H), 0.09 (s, 3H).

$^{13}$C NMR (75 MHz, CDCl$_3$): δ 156.3, 142.2, 142.1, 136.6, 136.5, 133.6, 133.5, 126.9, 126.8, 125.1, 125.0, 118.7, 118.6, 116.7, 116.6, 114.5, 114.4, 110.9, 98.8, 97.3, 85.7, 85.3, 81.3, 80.9, 76.4, 75.4, 68.9, 63.0, 62.7, 62.7, 62.4, 62.3, 35.0, 33.9, 33.3, 32.6, 32.0, 31.9, 31.2, 31.1, 29.7, 26.9, 25.9, 25.8, 25.4, 25.1, 24.6, 22.5, 20.1, 19.9, 18.2, 15.4, 14.7, 14.0, 13.9, −4.49, −4.48.

(M+Na): 605.6

Example 4

Synthesis of Compound (10α)

Dicobalt octacarbonyl (Co$_2$(CO)$_8$; 24.3 g) was added to the solution of compound (9α) (25 g) in 245 ml toluene and the reaction mixture was stirred at 25 to 30° C. for some time. The reaction mass was further heated to 70 to 80° C. and stirred at the same temperature till completion of the reaction as monitored by HPLC. After completion, the resultant mass was cooled to 10 to 30° C. and ammonium chloride solution (37.5 g in 250 ml water) was added to it with stirring. The mass was then filtered and organic layer was separated from the filtrate and concentrated to give a residue containing compound (10α). Cyclohexane (175 ml) was added to the residue and resulting mass was filtered. The filtrate was concentrated and the residue was subjected to chromatographic purification with cyclohexane/ethyl acetate as eluent to provide compound (10α). Yield: 24.5 g (95.9%)

$^1$H NMR (300 MHz, CDCl$_3$): δ7.21 (m, 1H), 6.92 (m, 1H), 6.76 (m, 1H), 6.03 (m, 1H), 5.48 (m, 2H), 5.26 (m, 1H), 4.49 (m, 3H), 3.84 (m, 1H), 3.51 (m, 2H), 3.34 (m, 2H), 2.68 (dd, J=14.0 and 6.3 Hz, 1H), 2.36-2.14 (m, 4H), 1.82-1.19 (m, 16H), 0.85 (m, 12H), 0.12 (s, 3H), 0.82 (s, 3H).

$^{13}$C NMR (75 MHz, CDCl$_3$): δ 209.4, 172.5, 155.8, 138.3, 137.2, 133.2, 127.3, 125.3, 122.0, 117.3, 117.2, 110.4, 110.2, 97.7, 76.3, 68.7, 65.4, 62.7, 42.1, 34.5, 33.6, 33.4, 33.3, 32.0, 31.9, 31.8, 31.3, 31.26, 31.21, 25.6, 25.5, 25.4, 25.1, 24.6, 25.5, 20.2, 19.9, 19.3, 18.7, 18.0, 14.0, 13.9, −4.1. (M+Na): 605.4

Example 5

Synthesis of Compound (16)

Compound (10α) (24 g) was added to the stirred solution of DMSO (100 ml) and morpholine (2.9 g), followed by addition of Pd(PPh$_3$)$_4$ (0.39 g). The reaction mixture was stirred at 25 to 45° C. till completion of reaction as monitored by TLC. After completion, water was added to the reaction mixture, followed by extraction with ethyl acetate. Separation and concentration of the organic layer provided a residue which was subjected to column chromatographic purification with a mixture of ethyl acetate and cyclohexane as eluent to give compound (16). Yield: 20.1 g (89.5%)

$^1$H NMR (300 MHz, CDCl$_3$): δ7.13 (m, 1H), 6.89 (m, 1H), 6.72 (m, 1H), 5.58 (s, 0.5H), 5.48 (s, 0.5H), 5.22 (bs, 1H), 4.50 (m, 1H), 3.78 (m, 1H), 3.48-3.37 (m, 4H), 2.69 (m, 1H), 2.46-2.13 (m, 4H), 1.81-1.20 (m, 16H), 0.88-0.82 (m, 12H), 0.14-0.08 (m, 6H).

$^{13}$C NMR (75 MHz, CDCl$_3$): δ 210.1, 209.9, 173.0, 172.9, 153.3, 138.7, 138.5, 137.6, 137.2, 127.4, 127.3, 123.0, 122.1, 121.9, 114.3, 114.0, 97.8, 97.7, 76.4, 76.3, 65.4, 65.2, 62.9, 62.6, 42.2, 34.5, 33.6, 33.3, 33.2, 33.1, 32.1, 31.9, 31.8, 31.3, 31.2, 26.9, 25.63, 25.61, 25.5, 25.4, 25.1, 24.6, 22.5, 20.1, 19.9, 19.3, 18.7, 18.0, 14.0, 14.0, −4.1, −4.3.

(M+Na): 565.4

Example 6

Synthesis of Compound (14)

Pd/C (5%, moisture 50%, 3.75 g) was added to the stirred mixture of compound (16) in ethanol (250 ml) and potassium carbonate (5 g) placed in an autoclave. The reaction mixture in the autoclave was stirred at 25 to 30° C. under hydrogen pressure (10 to 12 Kg/cm$^2$) and the reaction was continued till completion, as monitored by HPLC.

After completion, the reaction mixture was filtered and concentrated to give residue containing compound (17).

Aqueous sodium hydroxide solution (18.9 g NaOH in 94 ml water) was added to the solution of compound (17) in ethanol (250 ml), stirred at −5 to −10° C. Sodium borohydride (1.8 g) was then added to the mixture and stirring was continued at the same temperature.

After completion of the reaction, as monitored by HPLC, the reaction mixture was heated to 10 to 20° C. and acetic acid (40.5 ml) was added to it with stirring. The resulting mass was extracted with ethyl acetate. The organic layer was separated and concentrated to give a residue containing compound (18)

Methanol (125 ml) was added to the residue, followed by addition of para-toluene sulfonic acid monohydrate (0.9 g) at 25 to 30° C. The reaction mixture was stirred at 25 to 30° C. till completion as monitored by UPLC.

After completion of the reaction, aqueous sodium bicarbonate solution (5 g in 100 ml water) was added to the reaction mass. Partial concentration of the mixture maintaining temperature below 50° C., followed by addition of ethyl acetate (125 ml), stirring, separation and concentration of the organic layer provided compound (14). Yield: 10 g (81%)

$^1$H NMR (300 MHz, DMSO-D$_6$): δ 9.04 (s, 1H), 6.87 (t, J=5.8 Hz, 1H), 6.61 (d, J=5.5 Hz, 1H), 6.54 (d, J=5.4 Hz, 1H), 4.45 (d, J=4.1 Hz, 1H), 4.21 (t, J=4.0 Hz, 1H), 3.46 (m, 1H), 2.60 (m, 2H), 2.36 (m, 2H), 2.12 (m, 1H), 1.93 (m, 1H), 1.76 (m, 1H), 1.45-1.13 (m, 12H), 1.07-0.92 (m, 2H), 0.86 (t, J=5.2 Hz, 3H).

(M+Na): 355.7

Example 7

Synthesis of Compound (6β)

Ethyl magnesium bromide solution (143 ml, 3 M solution in tetrahydrofuran (THF) was gradually added to the solution of compound (5) (110 g) in dry THF, 1000 ml). The reaction mixture was stirred at 55 to 65° C. The mass was then cooled to −10 to 0° C., and solution of compound (4β) (73.2 g in 110 ml THF) was slowly added to it under stirring. The reaction was continued at −10 to 0° C. till completion of the reaction, as monitored by HPLC. After completion of the reaction, the reaction mixture was quenched with gradual addition of aqueous ammonium chloride solution (110 g ammonium chloride in 550 ml water). Ethyl acetate was added to the stirred reaction mixture and temperature was raised to 25 to 30° C. Separation and concentration of the organic layer gave crude mass which was subjected to column chromatographic purification with a mixture of cyclohexane/ethyl acetate as eluent to provide compound 6β. Yield: 120.2 g (70.8%)

Example 8

Synthesis of Compound 7β

Manganese dioxide (104.9 g) was added to the solution of compound (6β) (50 g in 225 ml toluene) and the reaction mixture was stirred at 45 to 50° C. till completion of the reaction, as monitored by HPLC. After completion, the reaction mixture was cooled, filtered, and concentrated to afford Compound (7β). Yield: 47 g (94.5%)

Example 9

Synthesis of Compound (9β)

The solution of (R)-(+)-2-Methyl-CBS-oxazaborolidine (103.2 ml, 1M solution in Toluene) was added to the stirred solution of Compound (7β) (35.5 g) in tetrahydrofuran (142 ml) at 25 to 30° C. and stirring was continued at the same temperature. The reaction mass was then cooled to −30 to −40° C. and borane-dimethyl sulfide complex (BH$_3$/DMS, 10 M, 17.2 ml) was added to it with continued stirring. The reaction was monitored by HPLC.

After completion of the reaction, the reaction mixture was warmed to −25 to −15° C. and methanol (71 ml) was slowly and cautiously added to it. The temperature of the reaction mass was raised to 25 to 30° C. followed by further stirring. The mixture was then cooled to 0 to 5° C. and ammonium chloride solution (5%, 177.5 ml) was added to it under stirring. The resulting mixture was extracted with methyl tertiary butyl ether. Separation and concentration of the organic layer gave a residue containing compound (8β)

Tertiary butyl dimethyl chlorosilane (TBDMSCl, 19.4 g) and imidazole (14.6 g) were added to the solution of Compound (8β) in dichloromethane (355 ml), DMF (3.6 ml) and 4-dimethyl amino pyridine (0.74 g). The reaction mixture was stirred at 25 to 30° C. After completion of the reaction, as monitored by HPLC, the reaction mixture was quenched with water and the organic layer was separated. Concentration of the organic layer followed by chromatographic purification yielded compound (9β). Yield: 40.0 g (88%)

Example 10

Synthesis of Compound (10β)

Dicobalt octacarbonyl (Co$_2$(CO)$_8$, 24.3 g) was added to the solution of compound (9β) (25 g) in 245 ml toluene and the reaction mixture was stirred at 25 to 30° C. for some time. The reaction mass was further heated to 70 to 80° C. and stirred at the same temperature till completion of the reaction as monitored by HPLC. After completion, the resultant mass was cooled to 10 to 30° C. and ammonium chloride solution (37.5 g in 250 ml water) was added to it with stirring. The mass was then filtered and organic layer was separated from the filtrate and concentrated to give a residue. Cyclohexane (175 ml) was added to the residue and resulting mass was filtered. The filtrate was concentrated and the residue was subjected to chromatographic purification with a mixture of cyclohexane/ethyl acetate as eluent to provide compound 10β. The fractions having desired compound were combined and concentrated to give residue containing compound (10β). Yield: 25.0 g (95%)

Example 11

Synthesis of Compound (13β)

Pd/C (5%, moisture 50%, 3.75 g) was added to the stirred mixture of Compound (10β), (25 g) in ethanol (250 ml) and potassium carbonate (5 g) placed in an autoclave. The reaction mixture in the autoclave was stirred at 25 to 30° C.

under hydrogen pressure (10 to 12 Kg/cm$^2$) and the reaction was continued till completion, as monitored by HPLC.

After completion, the reaction mixture was filtered and concentrated to give residue containing compound (11β).

Aqueous sodium hydroxide solution (18.9 g NaOH in 94 ml water) was added to the solution of Compound (11β) in ethanol (250 ml), stirred at −5 to −10° C. Sodium borohydride (1.8 g) was then added to the mixture and stirring was continued at the same temperature. After completion of the reaction, as monitored by HPLC, the reaction mixture was heated to 10 to 20° C. and acetic acid (40.5 ml) was added to it with stirring. The resulting mass was extracted with ethyl acetate. The organic layer was separated and concentrated to give a residue containing compound (12β).

Methanol (125 ml) was added to the residue, followed by addition of para-toluene sulfonic acid monohydrate (0.9 g) at 25 to 30° C. The reaction mixture was stirred at 25 to 30° C. till completion as monitored by UPLC.

After completion of the reaction, aqueous sodium bicarbonate solution (5 g in 100 ml water) was added to the reaction mass. Partial concentration of the mixture maintaining temperature below 50° C., followed by addition of ethyl acetate (125 ml), stirring, separation and concentration of the organic layer provided compound (13β). Yield: 12 g (76.9%).

Example 12

Synthesis of Compound (14)

Aluminium chloride (12.4 g) was gradually added to the stirred solution of compound (13β) (10.0 g) in dichloromethane (100 ml) and decanethiol (25.3 g) at 20 to 30° C. The resulting mixture was stirred at the same temperature till completion of the reaction as monitored by UPLC. After completion, the reaction mass was cooled to 0 to 10° C. Dilute hydrochloric acid (8 ml conc. HCl in 72 ml water) was added to it and the stirred solution was heated to 25 to 30° C. Further partial concentration of the mixture, extraction with ethyl acetate, separation and concentration of the organic layer gave a residue. Treatment of the residue with dichloromethane, methanol, stirring and filtration provided compound (14β). Yield: 7.0 g (73%).

Example 13

Synthesis of Treprostinil

Chloroacetonitrile (3.6 g) was gradually added to the mixture of compound (14) (6.0 g), acetone (100 ml) and potassium carbonate (10.4 g). The reaction mixture was stirred at 55 to 60° C. After completion of the reaction, as monitored by UPLC, reaction mixture was cooled to 35 to 40° C., and concentrated under vacuum. Water (70 ml) was added to the residue followed by addition of ethyl acetate and stirring. Separation and concentration of the organic layer after an optional treatment with activated carbon gave a residue containing compound 15β.

Methanol (50 ml) was added to the residue followed by addition of aqueous sodium hydroxide solution (4.8 g NaOH in 25 ml water). The reaction mixture was stirred at 55 to 60° C. till completion, as monitored by UPLC.

After completion, the reaction mixture was cooled to 40 to 45° C., and concentrated under vacuum. Water (30 ml) was added to the residue followed by addition of dilute hydrochloric acid (12 ml conc. HCl in 108 ml water) till the reaction mass attained pH between 8 and 10. Ethyl acetate was added to the stirred reaction mass and the organic layer was separated. Further acidification of the aqueous layer after an optional treatment with activated carbon, filtration, followed by treatment of the resulting solid with water, filtration and drying at 43-50° C. under reduced pressure gave Treprostinil. Yield: 6.5 g (93%), Purity: 99.89% (HPLC), Example 14

Synthesis of Treprostinil Sodium

Aqueous sodium hydroxide solution (1.1 g NaOH in 10 ml water) was added to Treprostinil (6 g) in water (20 ml) and the reaction mixture was stirred at 25 to 30° C. Filtration and lyophilization gave Treprostinil sodium. Yield: 6 gm (95%), Purity: 99.80%.

Example 15

Synthesis of Compound (2)

Meta hydroxy benzaldehyde (500 g) and potassium carbonate (679 g) were added to DMF (1000 ml). Allyl bromide (569.0 g) was gradually added to the reaction mixture, which was stirred at 25-45° C.

After completion of the reaction, water was added to the reaction mass followed by extraction with methyl tertiary butyl ether (MTBE). The organic layer was separated, washed with 1% sodium hydroxide solution (49 g NaOH in 490 ml water) to give compound (2). Yield: 630 g (94.8%)

Example 16

Synthesis of Compound (3)

Compound (2) (600 g) was added to decahydronaphthalene (1800 ml) and the stirred reaction mixture was heated to 180 to 190° C. Stirring was continued till completion of the reaction as monitored by HPLC. After completion, the reaction mixture was cooled and acetonitrile (4200 ml) was added to it. The acetonitrile layer was separated, concentrated. Toluene was added to the residue. The resulting mass was cooled, filtered. Optional treatment of the solid thus obtained using mixture of ethyl acetate and cyclohexane gave compound (3). Yield: 200 g (33.3%)

Example 17

Synthesis of Compound (4β)

Compound (3) (150 g) was added to the mixture of acetonitrile (750 ml) and potassium carbonate (192 g). The resultant mixture was stirred at 20 to 30° C. followed by gradual addition of dimethyl sulfate (128 g) at the same temperature. The reaction mass was stirred at 20 to 45° C., till completion, as monitored by HPLC. After completion, the reaction mixture was concentrated, and water (750 ml) was added to it. The resultant mass was stirred at 50 to 60° C., cooled and MTBE was added to it. The organic layer was separated and aqueous sodium hydroxide solution (14.8 g NaOH in 149 ml water was added to it with continuous stirring. Separation and concentration of the organic layer gave Compound (4β). Yield: 148 g (90.8%).

Example 18

Synthesis of Compound (4α)

Potassium carbonate (100 g) was added to the solution of compound (3) (100 g) in DMF (200 ml). Allyl bromide (86.8 g) was gradually added to the reaction mixture and the resulting mixture was stirred at 25 to 35° C.

After completion of the reaction, as monitored by TLC, the reaction mixture was quenched with water and extracted with methyl tertbutyl ether. The organic layer was concentrated to yield compound (4α). Yield: 110 g (88%).

$^1$H NMR (300 MHz, DMSO-D$_6$): δ 10.22 (s, 1H), 7.42 (m, 2H), 7.31 (dd, J=5.85 and 1.14 Hz, 1H), 5.91 (m, 2H), 5.39 (m, 1H), 5.25 (m, 1H), 4.89 (m, 2H), 4.63 (m, 2H), 3.83 (m, 2H).

M+H: 203.1

Example 19

Synthesis of Compound (AC-2)

S-(+)-Epichlorohydrin (100 g) was added to tetrahydrofuran (THF, 500 ml) and the mixture was stirred at 25 to 30° C. Copper iodide (20.6 g) was added to it, followed by slow, drop-wise addition of n-butylmagnesium chloride solution (513 ml, 2M solution in THF) to the reaction mass, which was stirred at −20 to −30° C.

After completion, as monitored by GC, ammonium chloride solution (300 g in 1000 ml water) was added to it. The reaction mixture was heated to room temperature under continued stirring. The reaction mixture was partially concentrated below 50° C., MTBE was added to the cooled mass and the organic layer was separated. Sodium hydroxide (86.5 g) was added to the organic layer containing AC-1 and the mixture was stirred at 25 to 30° C. till completion of the reaction as monitored by GC.

Filtration, concentration of MTBE layer provided compound (AC-2). Yield: 85 g (68.8%)

Example 20

Synthesis of Compound (AC-4)

AC-2 (50 g) was added to tetrahydrofuran (200 ml), at to 25 to 30° C., followed by addition of copper iodide (4.2 g). The reaction mass was cooled to 0 to −10° C. and allyl magnesium chloride solution (526 ml, 1M solution in THF) was added to it drop-wise. The reaction mixture was stirred at 0 to 10° C.

After completion of the reaction as monitored by GC, ammonium chloride solution (150 g in 500 ml water) was added to the reaction mass, temperature was raised to 25 to 30° C. The reaction mixture was stirred for some time, partially concentrated below 40° C., followed by addition of MTBE to the cooled mass. Stirring, separation and concentration of MTBE layer gave a residue containing compound (AC-3). Dichloromethane ((150 ml) was added to the residue, followed by addition of pyridinium p-toluene sulfonate (1.1 g) to the stirred mass. 2,3 dihydropyran (44.3 g) was further added gradually to the reaction mass. The reaction mixture was stirred at 25 to 30° C., till completion, as monitored by GC. After completion, the mass was quenched with water and extracted with dichloromethane. Separation, concentration of the organic layer gave a residue, which was subjected to chromatographic purification using a mixture of cyclohexane/ethyl acetate as eluent to provide compound (AC-4). Yield: 50.0 g (47.4%)

Example 21

Synthesis of Compound (5)

AC-4 (50 g) was added to dichloromethane (250 ml), followed by addition of pyridine (18.9 g). The reaction mixture was cooled to 0 to 5° C. and pyridine hydrobromide perbromide (73.2 g) was gradually added to it. The reaction was continued at 0 to 10° C. till completion, as monitored by GC. After completion, aqueous sodium thiosulphate solution (50 g sodium thiosulphate in 250 ml water) was added to the reaction mass with stirring. Separation, concentration of the organic layer gave a residue containing compound AC-5. Toluene (250 ml) was added to the residue followed by gradual addition of sodium amide (21.1 g) at 25 to 30° C. The reaction mixture was heated to 75 to 85° C. and stirring was continued till completion of the reaction as monitored by GC.

After completion, the reaction mixture was cooled to 0 to 10° C. and ammonium chloride solution (50 g in 250 ml water) was cautiously added to it The reaction mixture was heated to room temperature under continued stirring. Separation, concentration of the organic layer gave a residue which was subjected to chromatographic purification with a mixture of cyclohexane/ethyl acetate as eluent to provide compound (5). Yield: 27.0 g (54.4%).

The invention claimed is:

1. A process for the preparation of Treprostinil (1) and its pharmaceutically acceptable salts, comprising:

(a) reacting compound (4) with compound (5) to provide compound (6)

wherein R is alkyl (b) oxidizing compound (6) with MnO$_2$ and asymmetrically reducing resulting compound (7) to provide compound (8),

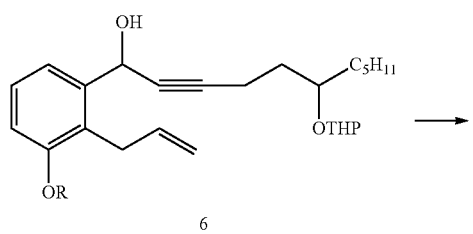

6

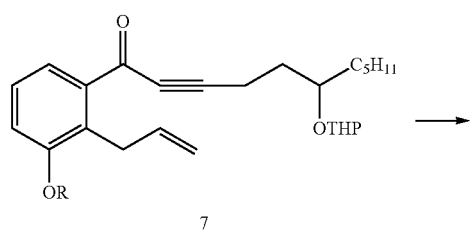

7

8

(c) treating compound (8) with a hydroxyl protecting reagent to give compound (9), cyclizing compound (9) in presence of dicobalt octacarbonyl (Co₂(CO)₈) to give compound (10), and hydrogenating to provide compound (11),

9

10

11

(d) treating compound (11) with a reducing agent to give compound (12), deprotecting the side-chain hydroxyl group in compound (12) to give compound (13), and treating compound (13) with a deprotecting agent to provide compound (14)

12

13

14

(e) treating compound (14) with halogenated acetonitrile to provide compound (15), converting compound (15) with alkaline hydrolysis followed by acidification to give Treprostinil (1) and its pharmaceutically acceptable salts,

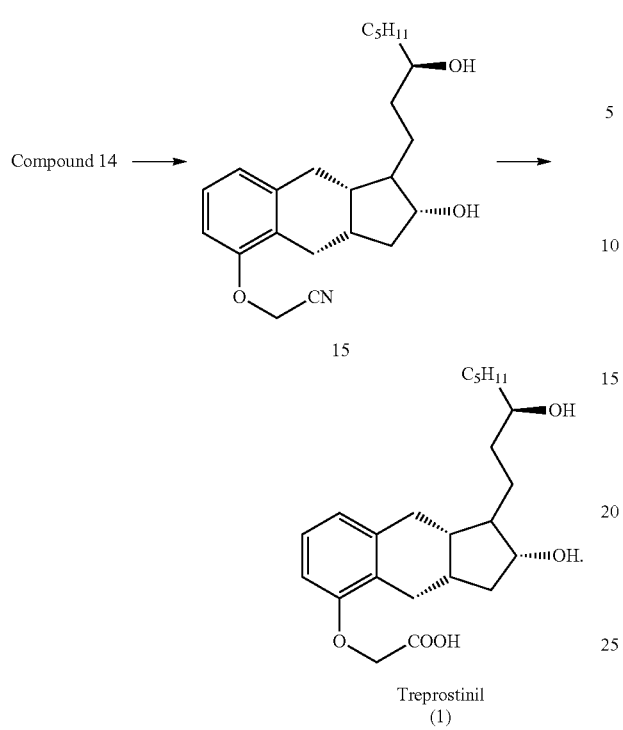

Treprostinil
(1)

2. The process according to claim 1 for the preparation of Treprostinil (1) and its pharmaceutically acceptable salts, comprising, treating compound (13) with a deprotecting agent to provide compound (14), further treating with halogenated acetonitrile to provide compound (15), converting compound (15) with alkaline hydrolysis followed by acidification to give Treprostinil (1) and its pharmaceutically acceptable salts.

3. The process according to claim 2 wherein compound (13) is treated with a reagent comprising a thiol derivative selected from ethanethiol, decanethiol, dodecanethiol and a Lewis acid selected from aluminium chloride and aluminium bromide.

4. A compound selected from the group consisting of compounds (6α), (7α), (8α) and (10α) and stereoisomers thereof:

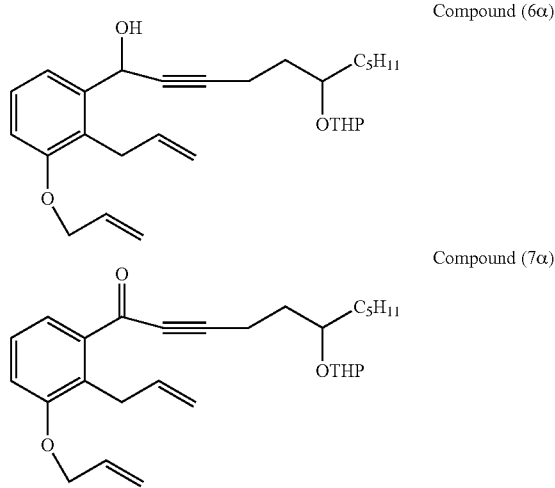

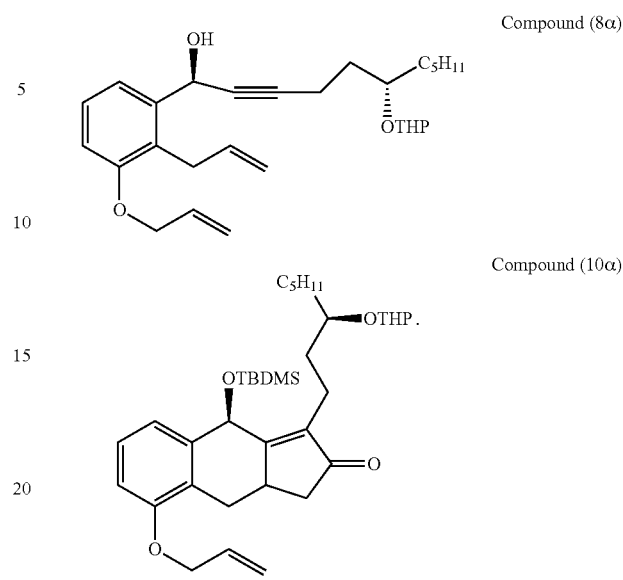

5. The process as claimed in claim 1 wherein compound (4) wherein R is alkyl, is synthesized by a process comprising, a) treating meta hydroxybenzaldehyde with allyl bromide in presence of potassium carbonate to provide compound (2), b) heating compound (2) between 160 and 210° C. in decahydronaphthalene as a solvent, adding acetonitrile after completion of reaction, separating the acetonitrile layer, concentrating the separated acetonitrile layer, adding a mixture of ethyl acetate and cyclohexane to the concentrated acetonitrile layer and isolating compound (3), c) treating compound (3) to give compound (4),

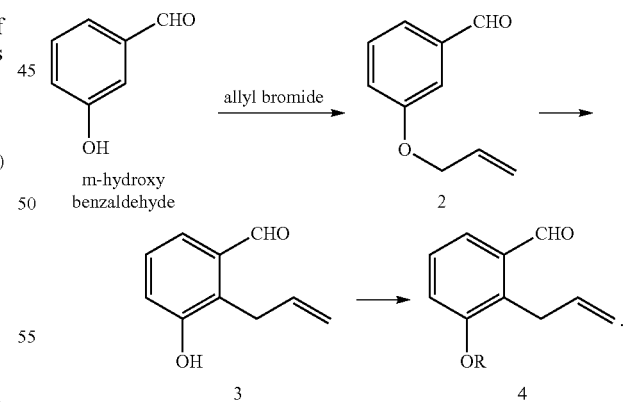

6. The process as claimed in claim 5 wherein compound (3) is treated with dimethyl sulfate to provide compound (4), wherein R is methyl.

7. A process for the preparation of Treprostinil (1) and its pharmaceutically acceptable salts, comprising:

(a) reacting compound (4) with compound (5) to give compound (6)

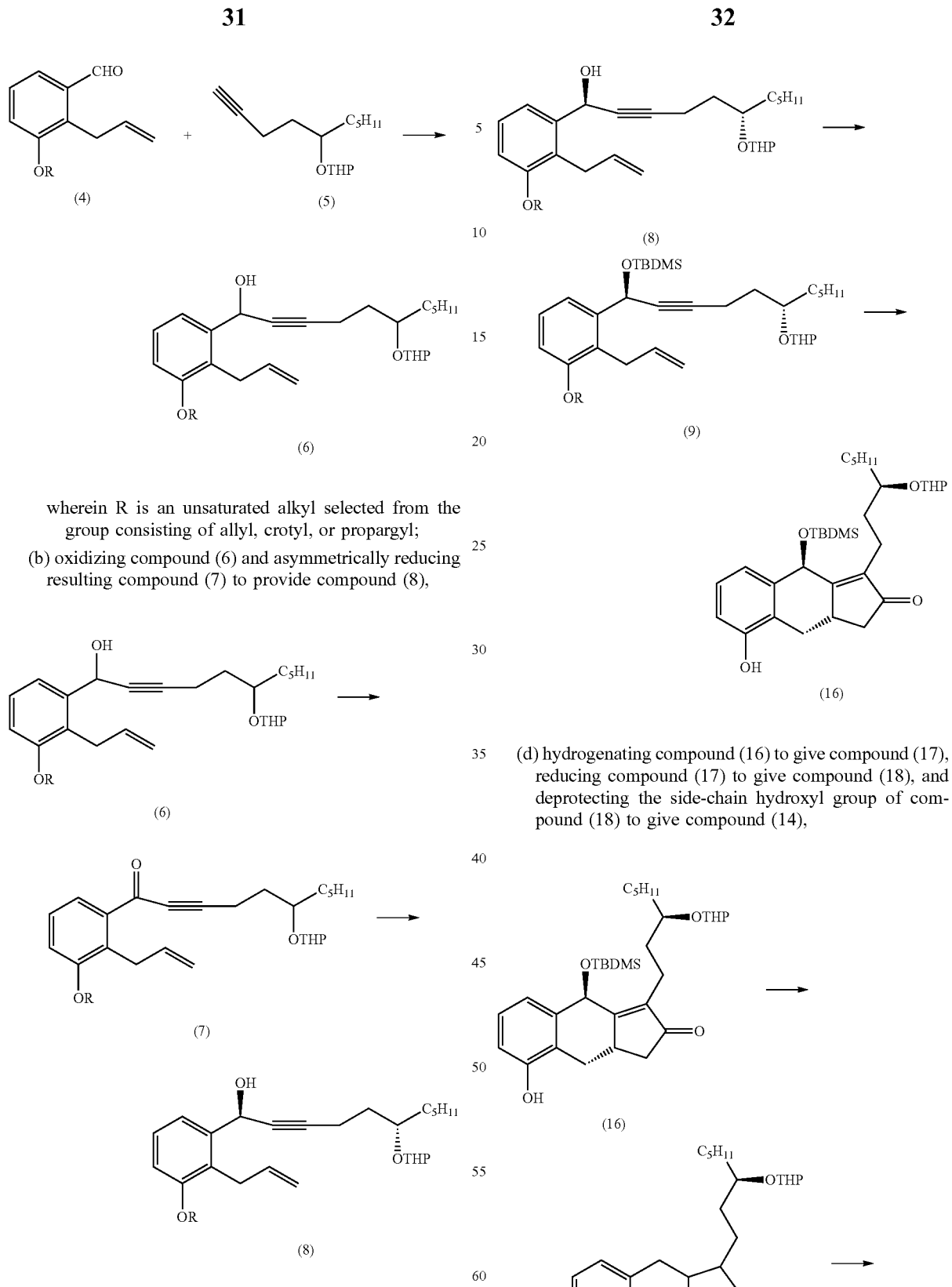

wherein R is an unsaturated alkyl selected from the group consisting of allyl, crotyl, or propargyl;

(b) oxidizing compound (6) and asymmetrically reducing resulting compound (7) to provide compound (8), (c) treating compound (8) with a hydroxyl protecting reagent to give compound (9), cyclizing compound (9) in presence of dicobalt octacarbonyl ($Co_2(CO)_8$) to yield compound (10), deprotecting the phenolic hydroxyl group in compound (10) to give compound (16)

(d) hydrogenating compound (16) to give compound (17), reducing compound (17) to give compound (18), and deprotecting the side-chain hydroxyl group of compound (18) to give compound (14), 33
-continued

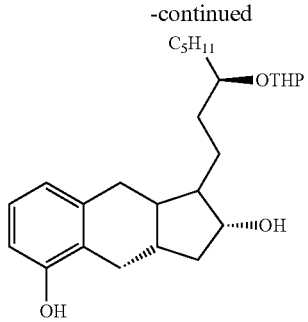
(18)

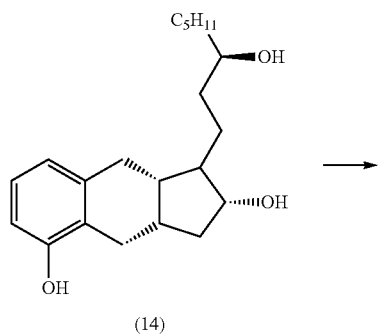
(14)

(e) treating compound (14) with halogenated acetonitrile to give compound (15), converting compound (15) with alkaline hydrolysis followed by acidification to give Treprostinil (1) and its pharmaceutically acceptable salts,

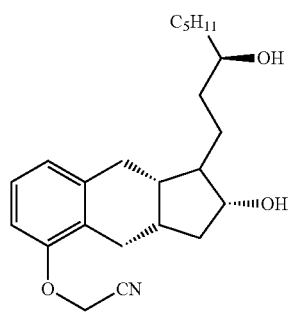
(14)

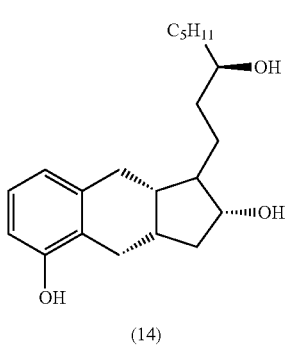
(15)

34
-continued

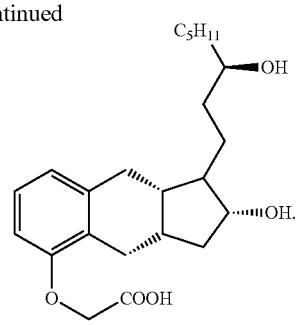
treprostinil (1)

8. The process according to claim 7 for the preparation of Treprostinil (1) and its pharmaceutically acceptable salts comprising, (a) reacting compound (4α) with compound (5) to give compound (6α),

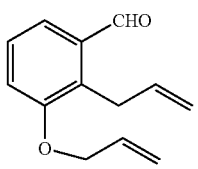
4α

5

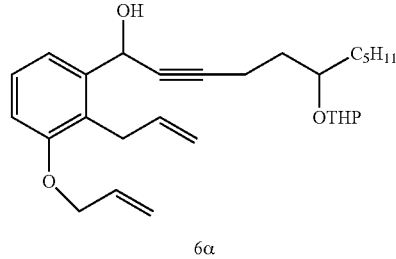
6α

(b) oxidizing compound (6α) and asymmetrically reducing resulting compound (7α) to provide compound (8α),

6α

7α

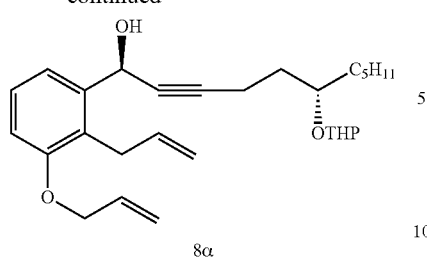

8α

(c) treating compound (8α) with a hydroxyl protecting reagent to give compound (9α), cyclizing compound (9α) in presence of dicobalt octacarbonyl (Co$_2$(CO)$_8$) to yield compound (10α), deprotecting the phenolic hydroxyl group in compound (10α) to give compound (16)

Compound 8α ⟶

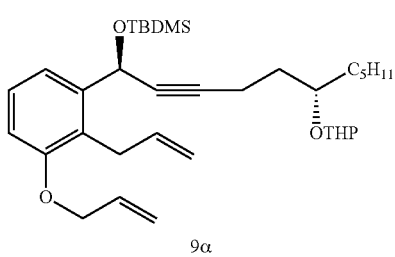

9α

$\xrightarrow{Co_2(CO)_8}$

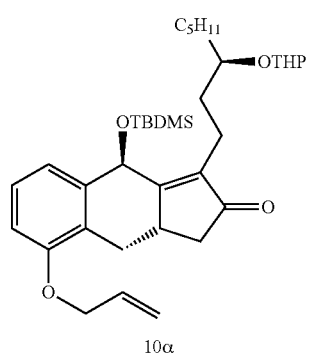

10α

16

(d) hydrogenating compound (16) to give compound (17), reducing compound (17) to give compound (18), and deprotecting the side-chain hydroxyl group of compound (18) to give compound (14), Compound 16 ⟶

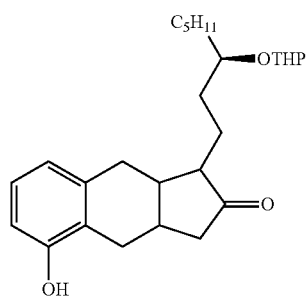

17

18

14

(e) treating compound (14) with halogenated acetonitrile to give compound (15), converting compound (15) with alkaline hydrolysis followed by acidification to give Treprostinil (1) and its pharmaceutically acceptable salts, Compound 14 ⟶

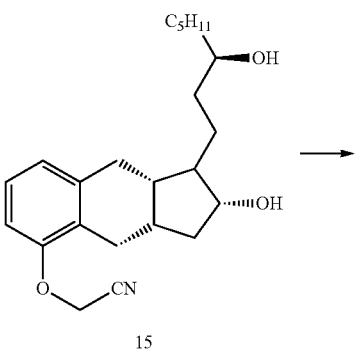

15

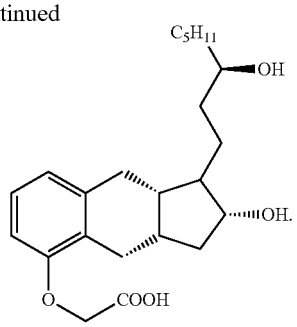

Treprostinil
(1)

9. The process according to claim 8 for the preparation of Treprostinil (1) and its pharmaceutically acceptable salts comprising, deprotecting the phenolic hydroxyl group in compound (10α) to give compound (16), hydrogenating compound (16) to give compound (17), reducing compound (17) to give compound (18), and deprotecting the side-chain hydroxyl group of compound (18) to give compound (14), treating compound (14) with halogenated acetonitrile to give compound (15), converting compound (15) with alkaline hydrolysis followed by acidification to give Treprostinil (1) and its pharmaceutically acceptable salts.

10. The process as claimed in claim 9, wherein the phenolic hydroxyl group is deprotected using $Pd(PPh_3)_4$/Morpholine, $Pd(PPh_3)_4$/$K_2CO_3$, or $Pd(PPh_3)_4$/sodium-2-ethylhexanoate.

11. The process as claimed in claim 7 wherein compound (4) wherein R is selected from the group consisting of allyl, crotyl, or propargyl, is synthesized by a process comprising, a) treating meta hydroxybenzaldehyde with allyl bromide in presence of potassium carbonate to provide compound (2),
b) heating compound (2) between 160 and 210° C. in decahydronaphthalene as a solvent, adding acetonitrile after completion of reaction, separating acetonitrile layer, concentrating the separated acetonitrile layer, adding a mixture of ethyl acetate and cyclohexane to the concentrated acetonitrile layer and isolating compound (3),
c) treating compound (3) to give compound (4),

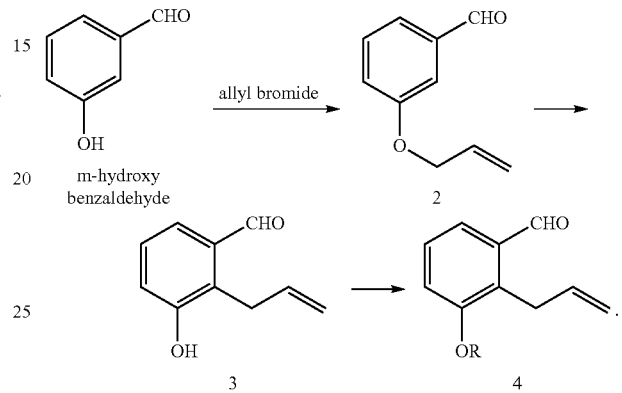

12. The process as claimed in claim 11 wherein compound (3) is treated with allyl bromide to provide compound (4), wherein R is allyl.

* * * * *